US009612156B2

(12) United States Patent
Sataka et al.

(10) Patent No.: US 9,612,156 B2
(45) Date of Patent: *Apr. 4, 2017

(54) SPECTROSCOPE AND MICROSPECTROSCOPIC SYSTEM

(71) Applicant: NIKON CORPORATION, Tokyo (JP)

(72) Inventors: Ryoichi Sataka, Yokohama (JP); Hisao Osawa, Kawasaki (JP)

(73) Assignee: NIKON CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/983,067

(22) Filed: Dec. 29, 2015

(65) Prior Publication Data

US 2016/0146669 A1 May 26, 2016

Related U.S. Application Data

(63) Continuation of application No. 14/448,334, filed on Jul. 31, 2014, now Pat. No. 9,243,955, which is a
(Continued)

(30) Foreign Application Priority Data

Feb. 6, 2012 (JP) ................................. 2012-022619

(51) Int. Cl.
*G01J 3/30* (2006.01)
*G01J 3/44* (2006.01)
(Continued)

(52) U.S. Cl.
CPC .......... *G01J 3/4406* (2013.01); *G01J 3/0205* (2013.01); *G01J 3/0208* (2013.01); *G01J 3/0237* (2013.01);
(Continued)

(58) Field of Classification Search
CPC ........ G01J 3/02; G01J 3/4406; G01N 21/718; G01N 21/645; G01N 21/6458
(Continued)

(56) References Cited

U.S. PATENT DOCUMENTS

| 5,371,624 A | 12/1994 | Nagano et al. |
| 5,852,498 A | 12/1998 | Youvan et al. |

(Continued)

FOREIGN PATENT DOCUMENTS

| JP | S61-6328 B2 | 2/1986 |
| JP | H05-188299 A | 7/1993 |

(Continued)

OTHER PUBLICATIONS

Mar. 19, 2013 International Search Report issued in International Patent Application No. PCT/JP2013/052443.
(Continued)

*Primary Examiner* — Abdullahi Nur
(74) *Attorney, Agent, or Firm* — Oliff PLC

(57) ABSTRACT

A spectroscope used for a microspectroscopic system includes: a collimating optical system that causes signal light to be substantially collimated light; spectroscopic optical systems and each of which includes at least one of each of spectral elements and in which a wavelength band for spectral separation varies depending on an incident angle of the signal light; at least one of each of optical receivers that detect the signal light spectrally separated by the spectroscopic optical systems; a mechanism that varies the incident angles of the signal light on the spectral elements; and a controller unit that determines the incident angles of the signal light on the spectral elements in accordance with the wavelength band for spectrally separating the signal light and controls the mechanism so as to attain the incident angles.

15 Claims, 13 Drawing Sheets

Related U.S. Application Data continuation of application No. PCT/JP2013/052443, filed on Feb. 4, 2013.

(51) Int. Cl.
    *G01N 21/64*     (2006.01)
    *G02B 21/00*     (2006.01)
    *G01J 3/02*     (2006.01)
    *G01J 3/12*     (2006.01)

(52) U.S. Cl.
    CPC ............ *G01J 3/0256* (2013.01); *G01N 21/64* (2013.01); *G02B 21/0064* (2013.01); *G02B 21/0076* (2013.01); *G01J 2003/1243* (2013.01); *G01N 21/6458* (2013.01); *G01N 2021/6419* (2013.01); *G01N 2021/6421* (2013.01)

(58) Field of Classification Search
    USPC .................................................. 356/300–334
    See application file for complete search history.

(56) References Cited

U.S. PATENT DOCUMENTS 6,909,542 B2     6/2005     Sasaki
2004/0239929 A1*   12/2004   Boehm ..................... G01J 3/14
    356/327
2005/0286048 A1   12/2005   Kitagawa
2008/0158549 A1*   7/2008   Lee ...................... G01N 21/553
    356/73

FOREIGN PATENT DOCUMENTS

| JP | H10-253452 A | 9/1998 |
|---|---|---|
| JP | 2000-249925 A | 9/2000 |
| JP | 2000-513102 A | 10/2000 |
| JP | 2002-267933 A | 9/2002 |
| JP | 2006-010944 A | 1/2006 |
| JP | 2008-061969 A | 3/2008 |

OTHER PUBLICATIONS

Mar. 19, 2013 Written Opinion issued in International Patent Application No. PCT/JP2013/052443.
Jul. 2, 2015 Office Action issued in Japanese Patent Application No. 2013-557499.
Mar. 3, 2015 Office Action issued in U.S. Appl. No. 14/448,334.
Sep. 15, 2015 Notice of Allowance issued in U.S. Appl. No. 14/448,334.
Notice of Reasons for Rejection dated Nov. 25, 2016 issued in corresponding Japanese Patent Application No. 2015-255332.

\* cited by examiner

SPECTROSCOPE AND MICROSPECTROSCOPIC SYSTEM

This is a Continuation of application Ser. No. 14/448,334 filed Jul. 31, 2014 (now U.S. Pat. No. 9,243,955), which in turn is a Continuation of International Application No. PCT/JP2013/052443 filed Feb. 4, 2013, which claims priority of Japanese Patent Application No. 2012-022619 filed Feb. 6, 2012. The disclosures of the prior applications are hereby incorporated by reference herein in their entireties.

TECHNICAL FIELD

The present invention relates to a spectroscope and a microspectroscopic system.

BACKGROUND ART

A conventional scanning fluorescence microscope is configured such that excitation light emitted from a point light source is scanned on a specimen by a scanning unit, fluorescence light emitted from the specimen excited by the excitation light is descanned with the scanning unit and spectrally separated with a filter, and furthermore, the spectrally separate fluorescence light is detected with optical receivers. In this case, in order to detect the fluorescence light emitted from the specimen efficiently, a number of filters are necessary to be prepared in accordance with excitation light and fluorescent dyes which are used by the user (for example, refer to Patent Literature 1).

CITATION LIST

Patent Literature

Patent Literature 1: U.S. Pat. No. 6,909,542

SUMMARY OF INVENTION

Technical Problem

However, in a conventional spectral separation method of using a filter, an acquisition region for a fluorescent wavelength is defined for each filter. Hence, an acquisition region for a fluorescent wavelength cannot be selected arbitrarily as needed and a proper filter should be reselected differently every time when the fluorescent dye is changed. Therefore, the device should have a number of filters, causing a cost to be high and the device to be large in dimensions, this being a problem.

The present invention is devised in view of such a problem and an object thereof is to provide a spectroscope and a microspectroscopic system in which a wavelength region of light which is spectrally separated and detected can be varied by varying an incident angle of fluorescence light on a spectral element which is an angle-dependent element to vary wavelength characteristics of the spectral element.

Solution to Problem

To solve the above-mentioned problem, a spectroscope according to the present invention includes: a collimating optical system that causes light to be substantially collimated light; a spectroscopic optical system including at least one spectral element in which a wavelength band for spectral separation varies depending on an incident angle of the light; at least one optical receiver that detects the light spectrally separated by the spectroscopic optical system; a mechanism that varies the incident angle of the light on the spectral element; and a controller unit that determines the incident angle of the light on the spectral element in accordance with the wavelength band for spectrally separating the light and controls the mechanism so as to attain the incident angle.

In such a spectroscope, the controller unit may control the mechanism to vary a direction of an incident surface of the spectral element.

Moreover, in such a spectroscope, the spectroscopic optical system may include an optical element that guides, corresponding to variation of an exiting angle of a part of the light spectrally separated by the spectral element, the part of the light to the optical receiver, the variation arising along with variation of the incident angle of the light on the spectral element.

Moreover, such a spectroscope may include the mechanism that moves the optical receiver correspondingly to variation of an exiting angle of a part of the light spectrally separated by the spectral element, the variation arising along with variation of the incident angle of the light on the spectral element.

Moreover, in such a spectroscope, the spectroscopic optical system may have a first optical element that transmits a part of the incident light and reflects the rest thereof, and a second optical element that reflects at least part of the light reflected by the first optical element, at least one of the first optical element and the second optical element may be the spectral element in which the wavelength band for spectral separation varies depending on the incident angle of the light, and the controller unit may control the mechanism to vary a direction of an incident surface of the first optical element and may control, in accordance with variation of the direction of the incident surface of the first optical element, the mechanism to vary a direction of an incident surface of the second optical element.

Moreover, in such a spectroscope, the controller unit may control the mechanism to vary the incident angle by moving the first optical element and the second optical element, maintaining an angle formed by a plane having the incident surface of the first optical element extended and a plane having the incident surface of the second optical element extended to be a predetermined value.

Moreover, such a spectroscope may control the mechanism to vary the incident angle by integrally rotating the first optical element and the second optical element around a line intersection, as an axis, of the plane having the incident surface of the first optical element extended and the plane having the incident surface of the second optical element extended.

Moreover, in such a spectroscope, the controller unit may control the mechanism to vary the incident angle by rotating the second optical element around a rotational axis, as a center, of the first optical element in accordance with rotation of the first optical element around the rotational axis which is positioned on an optical axis of the collimating optical system.

Moreover, such a spectroscope may include a condenser lens that collects the light exiting out of the second optical element on the optical receiver.

Moreover, such a spectroscope may include a barrier filter that is disposed between the spectroscopic optical system and the optical receiver which receives the light spectrally separated by the spectroscopic optical system and cuts light different in wavelength from the light, wherein in the barrier filter, a wavelength band of the cut light may vary depending on an incident angle of the light different in wavelength on the barrier filter.

Moreover, a microspectroscopic system according to the present invention comprises: a microscope that scans illumination light having a predetermined wavelength radiated from a light source to irradiate a specimen via an objective lens and collects, with the objective lens, the light which is radiated from the specimen and has a different wavelength from the predetermined wavelength; and any of the above-mentioned spectroscopes that spectrally separates and detects the light from the microscope.

In such a microspectroscopic system, the controller unit may control the mechanism so as to attain the incident angle correspondingly to at least one of a kind of a fluorescent dye, a wavelength of the illumination light and a wavelength of the light which are inputted by an input unit.

Moreover, such a spectroscopic system may include a storage unit that stores the incident angle in association with at least one of the kind of the fluorescent dye, the wavelength of the illumination light and the wavelength of the light, wherein the controller unit may control the mechanism so as to attain the incident angle read out from the storage unit.

Moreover, in such a spectroscopic system, the controller unit may control the mechanism based on a correction value, of the incident angle, which arises from switching the wavelength of the illumination light.

Advantageous Effects of Invention

According to the present invention, there can be provided a spectroscope and a microspectroscopic system in which a wavelength region of light which is spectrally separated and detected can be varied by varying an incident angle of signal light (fluorescence light) on a spectral element which is an angle-dependent element to vary wavelength characteristics of the spectral element.

BRIEF DESCRIPTION OF DRAWINGS

FIG. 3A illustrates wavelength characteristics of one spectral element and FIG. 3B illustrates wavelength characteristics in a case where two spectral elements are combined.

DESCRIPTION OF EMBODIMENTS

Figure 1:
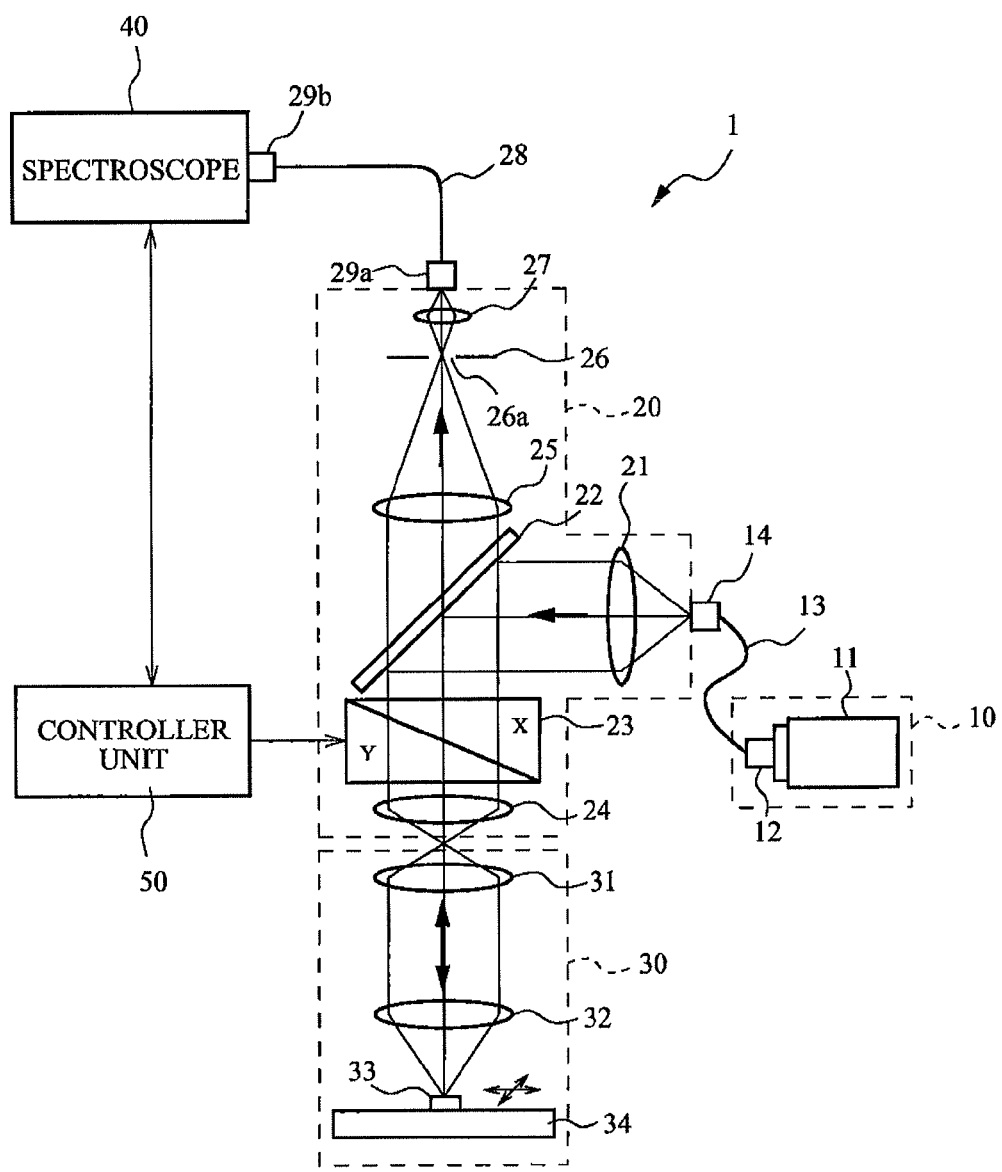
FIG. 1 is an explanatory drawing illustrating a configuration of a microspectroscopic system.

Hereafter, preferred embodiments of the present invention are described with reference to the drawings. First, a configuration of a microspectroscopic system is described using FIG. 1. As illustrated in FIG. 1, the microspectroscopic system 1 is configured to have a light source system 10, a confocal microscope having a confocal unit 20 and a microscope 30, a spectroscope 40 and a controller unit 50. In the microspectroscopic system 1, the confocal unit 20 and the spectroscope 40 are optically connected to each other with an optical fiber 28 via fiber couplers 29a and 29b.

The light source system 10 has a laser device 11, an optical fiber 13 and fiber couplers 12 and 14. The laser device 11 includes a laser diode, for example, and emits laser light (illumination light) having desired wavelength characteristics. The illumination light is guided to the confocal unit 20 via the optical fiber 13. Notably, in the example of FIG. 1, excitation light for exciting a specimen 33 and causing the same to emit fluorescence light is emitted as the illumination light.

The confocal unit 20 has a collimator lens 21 causing the illumination light from the light source system 10 to be substantially collimated light flux, a dichroic mirror 22, a scanning unit 23, a scanner lens 24, a condenser lens 25, a pinhole plate 26 having a pinhole 26a, and a relay lens 27. Moreover, the microscope 30 has a second objective lens 31, an objective lens 32 and a stage 34 on which the specimen 33 is placed. Combining the confocal unit 20 and the microscope 30 configures a scanning confocal microscope. Notably, the dichroic mirror 22 is configured to reflect laser light emitted from the light source system 10 to the microscope 30 side and to transmit fluorescence light radiated from the specimen 33 that has been excited by the laser light. Moreover, the focal point of the condenser lens 25 on the image side is disposed to coincide substantially with the pinhole 26a of the pinhole plate 26.

Laser light (illumination light) emitted from the laser device 11 of the light source system 10 is guided to the optical fiber 13 via the fiber coupler 12. Furthermore, the laser light having passed through the optical fiber 13 is incident on the collimator lens 21 of the confocal unit 20 through the fiber coupler 14. Then, after converted into substantially collimated light by the collimator lens 21, the laser light is reflected on the dichroic mirror 22 to the optical path on the microscope 30 side and guided to the scanning unit 23 constituted of two galvanomirrors which are arranged to be perpendicular to each other and the scanner lens 24, being two-dimensionally scanned. After caused to be substantially collimated light with the second objective lens 31, the scanned laser light is collected at one point on the specimen 33 with the objective lens 32. Notably, its position on the specimen 33 in two-dimensionally scanning with the scanning unit 23 is controlled by controlling operation of the galvanomirrors in the scanning unit 23 by the controller unit 50. Fluorescence light (signal light) radiated from the specimen 33 excited with the laser light (illumination light) is converted into substantially collimated light with the objective lens 32 and goes back along the reverse path to that for the laser light (illumination light) to be incident on the dichroic mirror 22. Furthermore, the fluorescence light incident on the dichroic mirror 22 passes through the dichroic mirror 22 and is collected on the pinhole 26*a* of the pinhole plate 26 by the condenser lens 25.

The fluorescence light (signal light) having passed through the pinhole 26*a* passes through the relay lens 27 and is guided to the optical fiber 28 through the fiber coupler 29*a*. Passing through the relay lens 27, as illustrated in FIG. 1, while allowed to be divergent light flux if left as it is, the light having passed through the pinhole 26*a* is collected again. Thus, it can be incident on an opening end of the optical fiber 28 effectively (with a small loss thereof) even in the case of an apparent small opening diameter.

Herein, a light convergence point formed in the pinhole 26*a* is an image of a light spot on the specimen 33. Hence, even when there is light emitted from any other point on the specimen 33, it is not imaged at the pinhole 26*a* but cut by the pinhole plate 26, almost not reaching the fiber coupler 29*a*. Therefore, only the light that can have passed through the pinhole 26*a* can reach the fiber coupler 29*a* through the relay lens 27. As a result, the scanning confocal microscope is a microscope which can observe a specimen not only with high horizontal resolution but also with high vertical resolution.

The fluorescence light (signal light) incident on the fiber coupler 29*a* passes through the optical fiber 28 and is guided into the spectroscope 40 through the fiber coupler 29*b*. Hereafter, a configuration of the spectroscope 40 according to the embodiment is described.

First Embodiment

Figure 2:
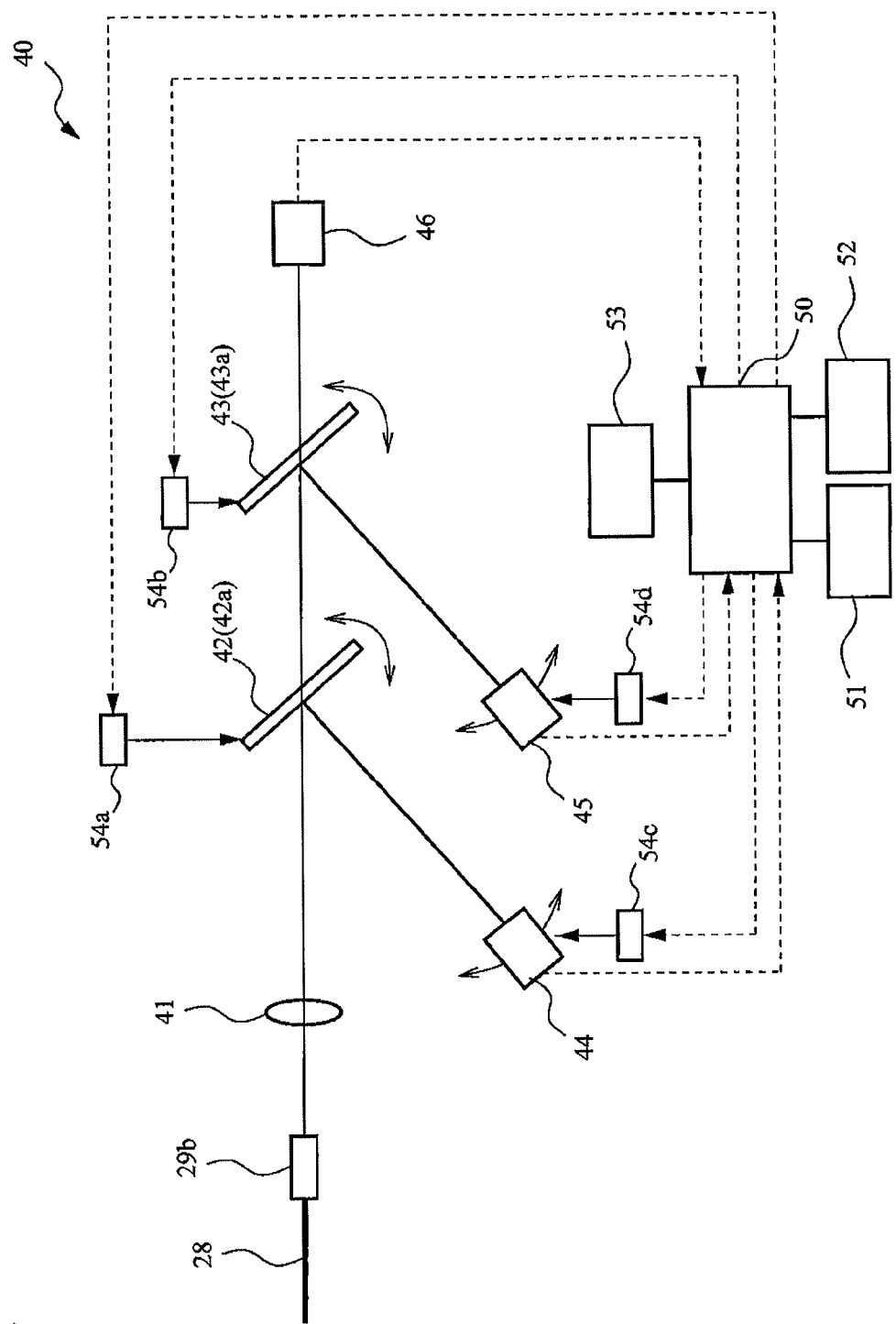
FIG. 2 is an explanatory drawing illustrating a configuration of a spectroscope according to a first embodiment.

As illustrated in FIG. 2, the spectroscope 40 is constituted of: a collimating optical system 41 causing the signal light incident from the optical fiber 28 through the fiber coupler 29*b* (fluorescence light in the example of FIG. 1) to be substantially collimated light flux; first and second spectroscopic optical systems 42 and 43 which are arranged on the optical axis of the collimating optical system 41, transmit a part of the incident signal light and reflect the rest thereof; a first optical receiver 44 detecting the intensity of the signal light which is reflected and spectrally separated on the first spectroscopic optical system 42; a second optical receiver 45 detecting the intensity of the signal light which passes through the first spectroscopic optical system 42 and is reflected and spectrally separated on the second spectroscopic optical system 43; and a third optical receiver 46 detecting the signal light which passes through and is spectrally separated on the second spectroscopic optical system 43.

Figure 3A:
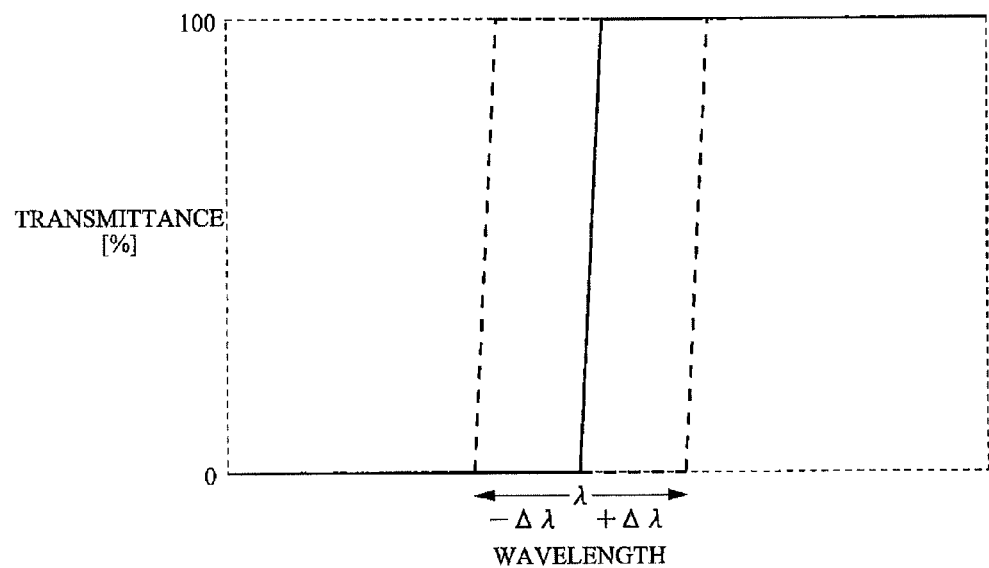
FIGS. 3A and 3B are an explanatory drawing for explaining wavelength characteristics of transmittance of spectral elements.

In the spectroscope 40, each of the first and second spectroscopic optical systems 42 and 43 is configured of one long path filter (spectral element 42*a* or 43*a*) which reflects light with shorter wavelength than a predetermined wavelength λ and transmits light with longer wavelength than the wavelength λ, for example, as illustrated in FIG. 3A (hereinafter, such a wavelength λ is referred to as "boundary wavelength"). Moreover, the spectral elements 42*a* and 43*a* constituting the first and second spectroscopic optical systems 42 and 43 are angle-dependent elements and each of them changes in boundary wavelength λ of transmission and reflection depending on an incident angle of the incident light (the case of FIG. 3A represents a case of being changeable from λ−Δλ to λ+Δλ).

Figure 3B:
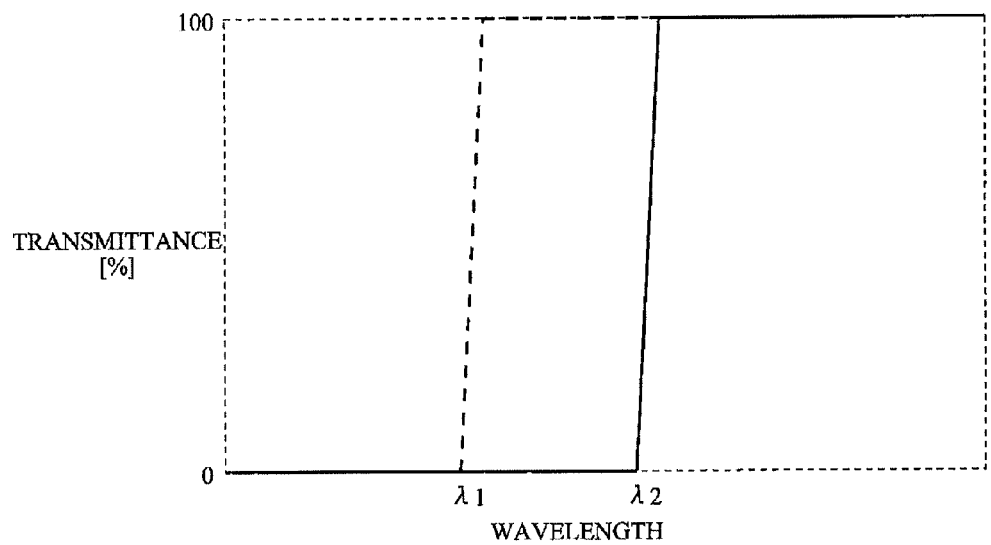

When two spectral elements 42*a* and 43*a* are combined as illustrated in FIG. 2, as illustrated in FIG. 3B, light with shorter wavelength than λ1 is reflected with the spectral element 42*a* of the first spectroscopic optical system 42 and detected by the first optical receiver 44, light with wavelength longer than λ1 and shorter than λ2 is reflected with the spectral element 43*a* of the second spectroscopic optical system 43 and detected by the second optical receiver 44, and light with longer wavelength than λ2 is detected by the third optical receiver 46, where a boundary wavelength of the first spectroscopic optical system 42 (spectral element 42*a*) is λ1 and a boundary wavelength of the second spectroscopic optical system 43 (spectral element 43*a*) is λ2. Here, each of the spectral elements 42*a* and 43*a* is rotated around an axis in a direction perpendicular to the optical axis (direction perpendicular to the plane of FIG. 2), and thereby, an incident angle of the incident signal light on each of the spectral elements 42*a* and 43*a* is varied. Thus, the boundary wavelengths λ1 and λ2 can be varied to adjust wavelength bands for the signal light detected by the respective first to third optical receivers 44 to 46. That is, in the spectroscope 40 according to the first embodiment, the first and second spectroscopic optical systems 42 and 43 are not necessary to be prepared to have boundary wavelengths different for each wavelength band of the signal light to be detected. Rotating the spectral elements 42*a* and 43*a* can adjust the wavelength bands for the spectrally separated signal light.

Notably, when the incident angles of the incident signal light are varied by rotating the spectral elements 42*a* and 43*a*, exiting angles at which it is reflected to exit also vary. Therefore, as illustrated in FIG. 2, in accordance with rotation of the spectral elements 42*a* and 43*a*, the first and second optical receivers 44 and 43 are necessary also to be rotated around the rotation centers of the spectral elements 42*a* and 43*a*.

Moreover, the spectroscope 40 with the configuration as above can be configured to be provided with drive units 54*a* to 54*d* as a mechanism for moving the spectral elements 42*a* and 43*a* (mechanism for varying the incident angles of the light with respect to the spectral elements 42*a* and 43*a*), so that the spectral elements 42*a* and 43*a* of the first and second spectroscopic optical systems 42 and 43 are rotated and the first and second optical receivers 44 and 45 are rotated with the drive units 54*a* to 54*d*, and can be configured to perform control of the rotation in response to a control signal from the controller unit 50.

As illustrated in FIG. 2, the controller unit 50 is connected to: an input unit 51 for inputting information for controlling operation of the first and second spectroscopic optical systems 42 and 43 and the first and second optical receivers 44 and 45; an output unit 52 displaying images of the specimen 33 detected by the first to third optical receivers 44 to 46; a storage unit 53 storing the images, control information and the like; and a mechanism constituted of the drive unit 54*a* moving (rotating) the spectral element 42*a* of the first spectroscopic optical system 42, the drive unit 54*b* moving (rotating) the spectral element 43*a* of the second spectroscopic optical system 43, the drive unit 54*c* moving the first optical receiver 44, and the drive unit 54*d* moving the second optical receiver 45. With respect to the controller unit 50, ranges of wavelengths for which the first to third optical receivers 44 to 46 perform detection (boundary wavelengths λ1 and λ2 of the spectral elements 42*a* and 43*a* actually) are configured to the controller unit 50 via the input unit 51, rotational angles of the spectral elements 42a and 43a (incident angles of the signal light on the spectral elements 42a and 43a) are determined so as to attain the boundary wavelengths by the controller unit 50, and moreover, rotational angles of the first and second optical receivers 44 and 45 are determined depending on those rotational angles to actuate the spectral elements 42a and 43a and the optical receivers 44 and 45 with the drive units 54a to 54d. Otherwise, it may be configured such that wavelengths (excitation wavelengths) of illumination light for exciting fluorescent dyes and wavelengths (fluorescent wavelengths) of signal light arising from the excited dyes are stored in the storage unit 53 in association with the individual fluorescent dyes, that necessary information is read out from the storage unit 53 by the controller unit 50 based on a kind of the fluorescent dye and the excitation wavelength or fluorescent wavelength inputted from the input unit 51 to determine the boundary wavelengths of the first and second spectroscopic optical systems 42 and 43, and that operation of the first and second spectroscopic optical systems 42 and 43 and the first and second optical receivers 44 and 45 is controlled by the drive units 54a to 54d so as to attain the determined boundary wavelengths. Undoubtedly, the incident angles of the signal light on the spectral elements 42a and 43a may be beforehand stored in the storage unit 53 in association with the fluorescent dyes and the like as mentioned above, so that the incident angles are read out to control operation of the first and second spectroscopic optical systems 42 and 43 and the like with the drive units 54a to 54d. Otherwise, correction values from the reference incident angles for each fluorescent dye may be stored in the storage unit 53, so that the rotational angles of the spectral elements 42a and 43a and the like are controlled in association with the correction values with the drive units 54a to 54d. Furthermore, when the wavelength of illumination light radiated from the laser device 11 of the light source system 10 is switchable, it may be configured such that wavelengths of illumination light radiated from the light source system 10 are stored in the storage unit 53 in association with the fluorescent dyes, the absorption wavelengths or the fluorescent wavelengths as mentioned above, so that operation of the first and second spectroscopic optical systems 42 and 43 and the like is controlled with the drive units 54a to 54d.

Figure 4:
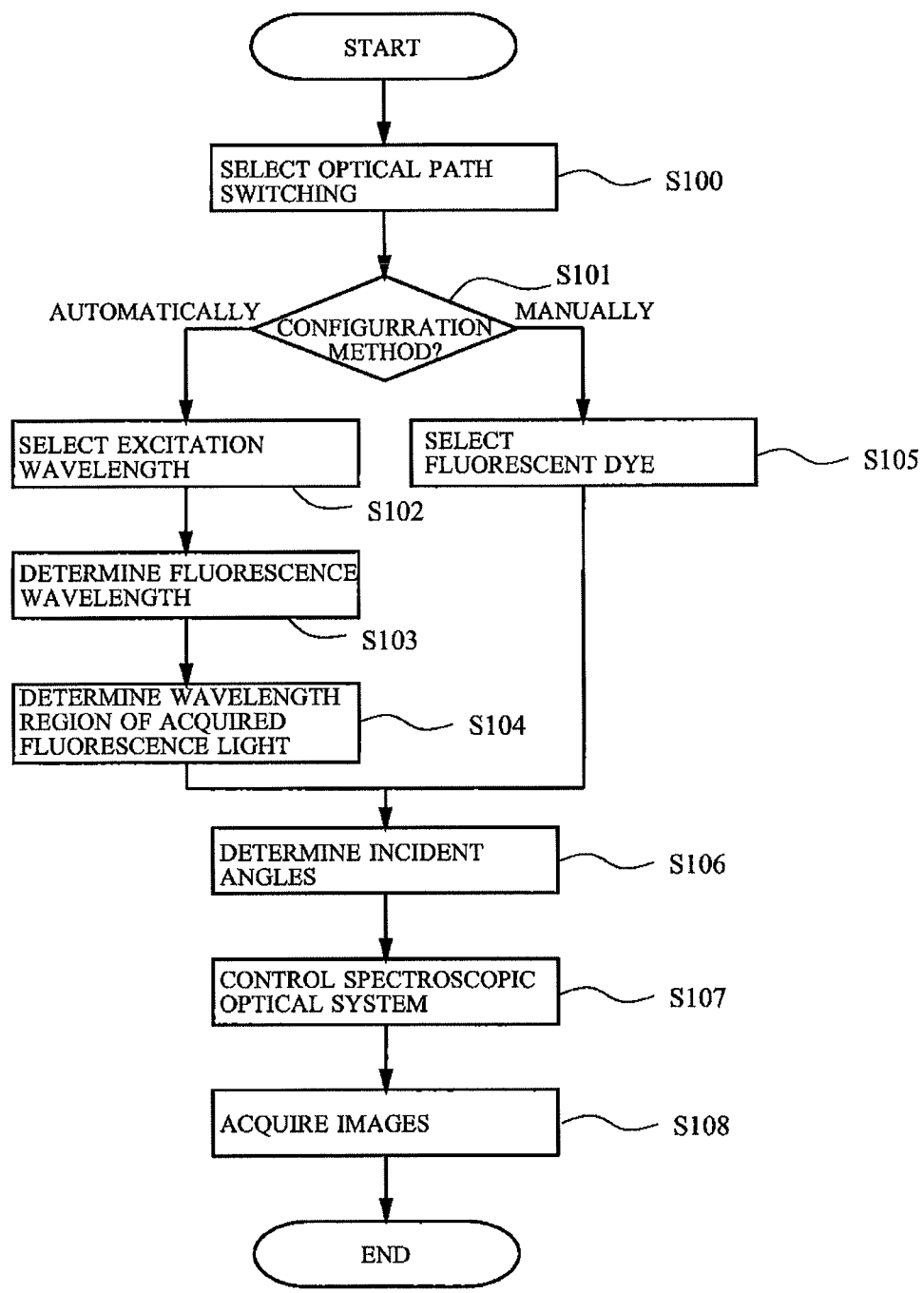
FIG. 4 is a flowchart illustrating processing in the occasion of acquiring images of a specimen by the microspectroscopic system.

Processing of the controller unit 50 in the microspectroscopic system 1 with the configuration as above is exemplarily described using the FIG. 4. When optical path switching is selected by the input unit 51 (step S100), a configuration method is determined (step S101). When manual configuration is selected, an excitation wavelength is selected (step S102). A selection method of the excitation wavelength can include direct input from the input unit 51 as mentioned above, or selection from wavelengths of illumination light radiated from the light source system 10. Then, the fluorescent wavelength corresponding to the excitation wavelength is selected from the storage unit 53 to be determined (step S103). A wavelength region of the fluorescent light to be acquired (boundary wavelengths λ1 and λ2 of the spectral elements 42a and 43a) is determined (step S104). Meanwhile, when it is determined that automatic configuration is selected in step S101, a fluorescent dye is caused to be selected with the input unit 51 (step S105).

Next, the rotational angles of the spectral elements 42a and 43a constituting the first and second spectroscopic optical systems 42 and 43 and the rotational angles of the first and second optical receivers 44 and 45 are determined based on the wavelength region of the fluorescence light to be acquired or the fluorescent dye determined as mentioned above (step S106). A determination method of the rotational angles can include calculating them by operations using operational expressions mentioned later, or calculating them beforehand for each fluorescent dye and each acquisition wavelength region to be stored in the storage unit 53 and reading out their values. Then, based on the obtained rotational angles, the first and second spectroscopic optical systems 42 and 43 and the first and second optical receivers 44 and 45 are controlled in regard to their operation with the drive units 54a to 54d (step S107), and when they come to predetermined positions, images of the specimen 33 are acquired from the first to third optical receivers 44 to 46 (step S108). The acquired images of the specimen 33 may be displayed on the output unit 52 or may be stored in the storage unit 53.

Notably, the control method using the mechanism of the spectroscopic optical system (drive units 54a to 54d) as above holds true for the following embodiments.

Moreover, while the spectroscope 40 according to the first embodiment illustrated in FIG. 2 is described as to a case where it is configured of the two spectral elements 42a and 43a and the first to third optical receivers 44 to 46 receiving the signal light that is reflected on or has passed through those and is spectrally separated, the number of the spectral elements is not limited to that in this embodiment but may be one or three or more. Moreover, the optical receivers can also be decreased or increased depending on the number of the spectral elements. Notably, since all of the spectrally separated light is not necessarily detected by the optical receivers, at least one or more optical receiver is sufficient.

Moreover, in the above-mentioned microspectroscopic system 1, there is a case where the excitation light that has excited the specimen 33 is reflected on the specimen 33 and is incident on the spectroscope 40 along with the signal light (fluorescence light). Therefore, in order to remove the excitation light from the signal light, an excitation light cutoff filter (barrier filter) may be disposed. In this case, when the excitation light cutoff filter is an angle-dependent element, rotating it to vary its incident angle allows a wavelength for the removal to be adjusted depending on an excitation light wavelength.

Furthermore, since the spectroscope 40 has the fiber coupler 29b of the optical fiber 28 as its incident end, it can be easily connected to the confocal microscope. As mentioned above, the confocal microscope performs the optical detection with the optical detector coupled to the pinhole. Causing the light that has passed through the pinhole to be incident onto the optical fiber enables introduction of the light into the spectroscope to be easily performed with the optical fiber. In this way, the spectroscope suitable for the confocal microscope with a function of spectral separation can be configured.

Second Embodiment

Figure 5:
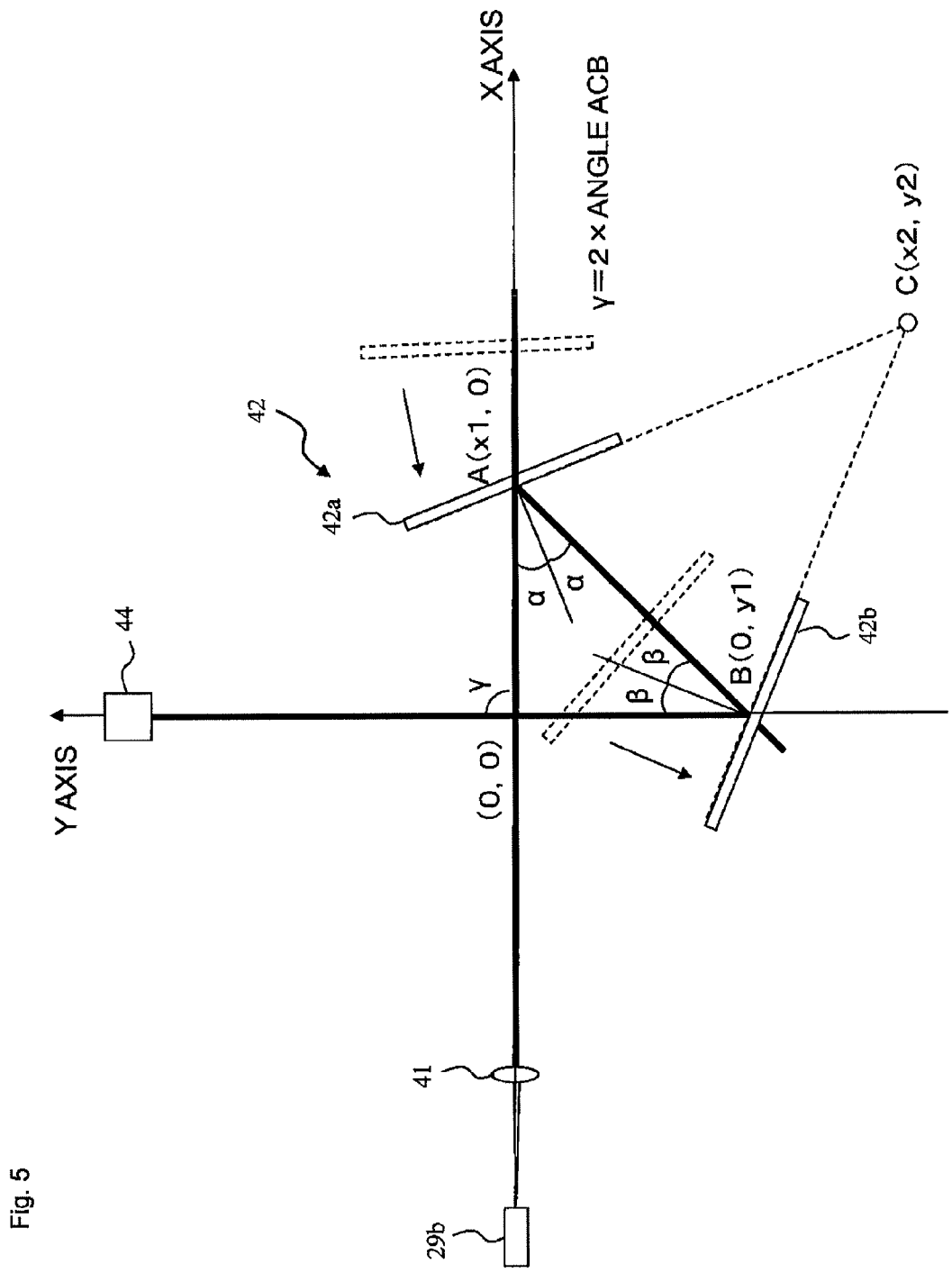
FIG. 5 is an explanatory drawing illustrating a configuration of a spectroscope according to a second embodiment.

When the spectroscope 40 according to the first embodiment is configured to have the configuration as illustrated in FIG. 2, it is necessary that the first and second optical receivers 44 and 45 that detect the signal light reflected on the spectral elements 42a and 43a are also rotated in accordance with rotation of the spectral elements 42a and 43a as mentioned above. Therefore, as illustrated in FIG. 5, each of the spectroscopic optical systems can be configured of two optical elements, so that the spectrally separated signal light is guided to the optical receiver that is fixedly disposed. For example, in the case of the first spectroscopic optical system 42 of the spectroscope 40 with the configuration in FIG. 2, as illustrated in FIG. 5, it is configured of a first optical element 42a which is arranged on the optical axis of the collimating optical system 41, transmits a part of the incident signal light and reflects the rest thereof, and a second optical element 42b which further reflects the reflected signal light out of the incident signal light on the first optical element 42a and guides it to the first optical receiver 44. Herein, the first optical element 42a is configured of the above-mentioned spectral element (for example, being a long path filter, and being an angle-dependent element). Moreover, the second optical element 42b is configured of a mirror. The first and second optical elements 42a and 42b are fixed in regard to relative positions between them and these optical elements 42a and 42b are rotated around an axis C (axis extending perpendicular to the plane of FIG. 5) as the center which is on the extension lines of the incident surfaces (reflective surfaces) of the two optical elements 42a and 42b and at which they intersect each other. Thereby, while the incident angles of the signal light on the first and second optical elements 42a and 42b vary, the spectrally separated signal light can be caused to be incident on the first optical receiver 44 that is fixedly disposed, irrespective of the changes in the incident angle.

Herein, positional relation between the first optical element 42a and the second optical element 42b is described. Notably, the description is made in which the optical axis of the collimating optical system 41 is an X-axis and an axis which passes through the center of the first optical receiver 44 in the direction perpendicular to the X-axis (upward/downward direction in the plane of FIG. 5) is a Y-axis.

The incident angle of the signal light on the first optical element 42a is represented as α and the incident position thereof is represented as A. The incident angle of the signal light reflected on the first optical element 42a on the second optical element 42b is represented as β and the incident position thereof is represented as B. Moreover, the intersection of the straight line which is parallel to the incident surface of the first optical element 42a and passes through point A with respect to the straight line which is parallel to the incident surface of the second optical element 42b and passes through point B is represented as C and the exiting angle of exiting from the second optical element 42b is represented as γ (herein, the angle formed by the ray reflected on the second optical element 42b relative to the optical axis of the collimating optical system 41 is defined as an exiting angle γ and the same holds true for the following description). As mentioned above, the first optical element 42a and the second optical element 42b rotate, holding the angle ACB to be constant. The exiting angle γ here is represented as in expression (1) below.

$$\gamma = 2\alpha + 2\beta \quad (1)$$

Moreover, since the sum of the interior angles of a triangle ABC is 180 degrees, relation between the incident angles α and β is represented as in expression (2) below and the exiting angle γ is represented as in expression (3) below.

Angle BAC+angle ABC+angle ACB=180

Angle BAC=90−α, angle ABC=90−β

$$\alpha + \beta = \text{angle } ACB \quad (2)$$

$$\gamma = 2 \times \text{angle } ACB \quad (3)$$

Therefore, even when the incident angle α varies, the exiting angle γ takes the constant value at all times. Notably, since the angle ACB is in the relation as in expression (3), when the angle ACB is set to 45 degrees, the exiting angle γ can be 90 degrees at all times for any incident angle α. In a preferable mode in view of the spectroscope 40 according to the second embodiment to be small in dimensions, the exiting angle γ is 90 degrees.

Moreover, the first optical element 42a is moved such that the positional point A which is predetermined on the incident surface of the first optical element 42a intersects the optical axis (X-axis) of the collimating optical system 41. Furthermore, the second optical element 42b is preferable to be moved such that the positional point B which is predetermined on the incident surface of the second optical element 42b is on the straight line (Y-axis) forming an angle relative to the optical axis (X-axis) of the collimating optical system 41 to be γ, in order that the reflected light from the first optical element 42a is caused to reach it with the angle ACB formed by the first optical element 42a and the second optical element 42b being constant.

Here, the coordinates of the incident position A of the first optical element 42a are (x1, 0) and the coordinates of the incident position B of the second optical element 42b are (0, y1) (y1<0), where the intersection of the X-axis and the Y-axis is the original, the first optical element 42a side is positive and the first optical receiver 44 side is positive, satisfying conditional expression (4) below.

$$y1/x1 = -\tan 2\alpha \quad (4)$$

Furthermore, the first optical element 42a and the second optical element 42b may be rotated around the coordinates of the intersection C, as the center, which satisfies the expression below with the angle ACB formed by the first optical element 42a and the second optical element 42b being constant. Herein, the coordinates of the intersection C, to be (x2, y2), satisfy conditional expression (5) below.

$$y2/x2 = 1 \quad (5)$$

Third Embodiment

Figure 6:
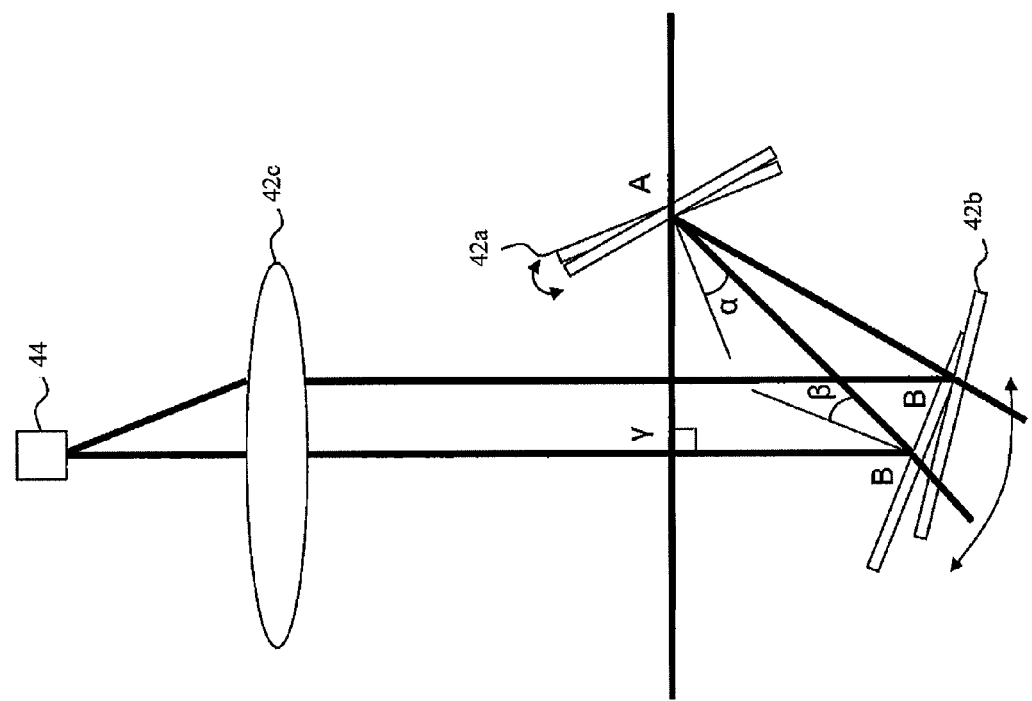
FIG. 6 is an explanatory drawing illustrating a configuration of a spectroscope according to a third embodiment.

In the configuration in which the spectroscopic optical system is configured of the two optical elements (first and second optical elements 42a and 42b) and the signal light spectrally separated by these optical elements is caused to be reflected and received, as illustrated in FIG. 6, a method in which the exiting angle γ is caused to be constant at all times even when the first spectral element 42a is rotated to vary the boundary wavelength can include a configuration in which, with respect to the first optical element 42a which rotates on the optical axis of the collimating optical system 41, the second optical element 42b is rotated around the rotational center A of the first optical element 42a, as the center (point B on which the signal light is incident is moved on the circumference of a circle with point A as its center). It should be noted that the light reflected on the second optical element 42b is caused to be shifted along the optical axis of the collimating optical system 41 in the case of such a configuration. Therefore, in order that the reflected light is caused to be incident on the fixedly disposed first optical receiver 44, a condenser lens 42c is necessary as illustrated in FIG. 6. Herein, the first optical receiver 44 is disposed at the focal point of the condenser lens 42c.

Notably, setting a movement distance of the position B of the incident signal light on the second optical element 42b as L, NA and a focal distance at least necessary for the condenser lens 42c satisfy relation as in expressions (6) and (7) below.

$$f \geq L \quad (6)$$

$$NA \geq L/f \quad (7)$$

By holding the relation above, even when the incident angle β on the first optical element 42a and the second optical element 42b varies in the third embodiment, the light can be received without moving the first optical receiver 44.

In such a configuration, since the optical receiver is not necessary to be moved unlike that in the first embodiment, the miniaturization of spectroscope 40 in dimensions can be attained. Notably, while moving the spectral element (first optical element 42a) is exemplarily described as a method of varying the incident angle of the light on the spectral element, not limited to this, a configuration in which the light is moved may be applied.

EXEMPLARY EMBODIMENTS

Now, an observation method of a specimen using the above-mentioned spectroscope is described. Notably, in the following exemplary embodiments, the cases where the spectroscopic optical system is configured of two optical elements and at least one of the optical elements is an angle-dependent element as illustrated in the second embodiment are exemplarily described. Meanwhile, the configuration illustrated in the first or third embodiment can be applied.

First Exemplary Embodiment

Figure 7:
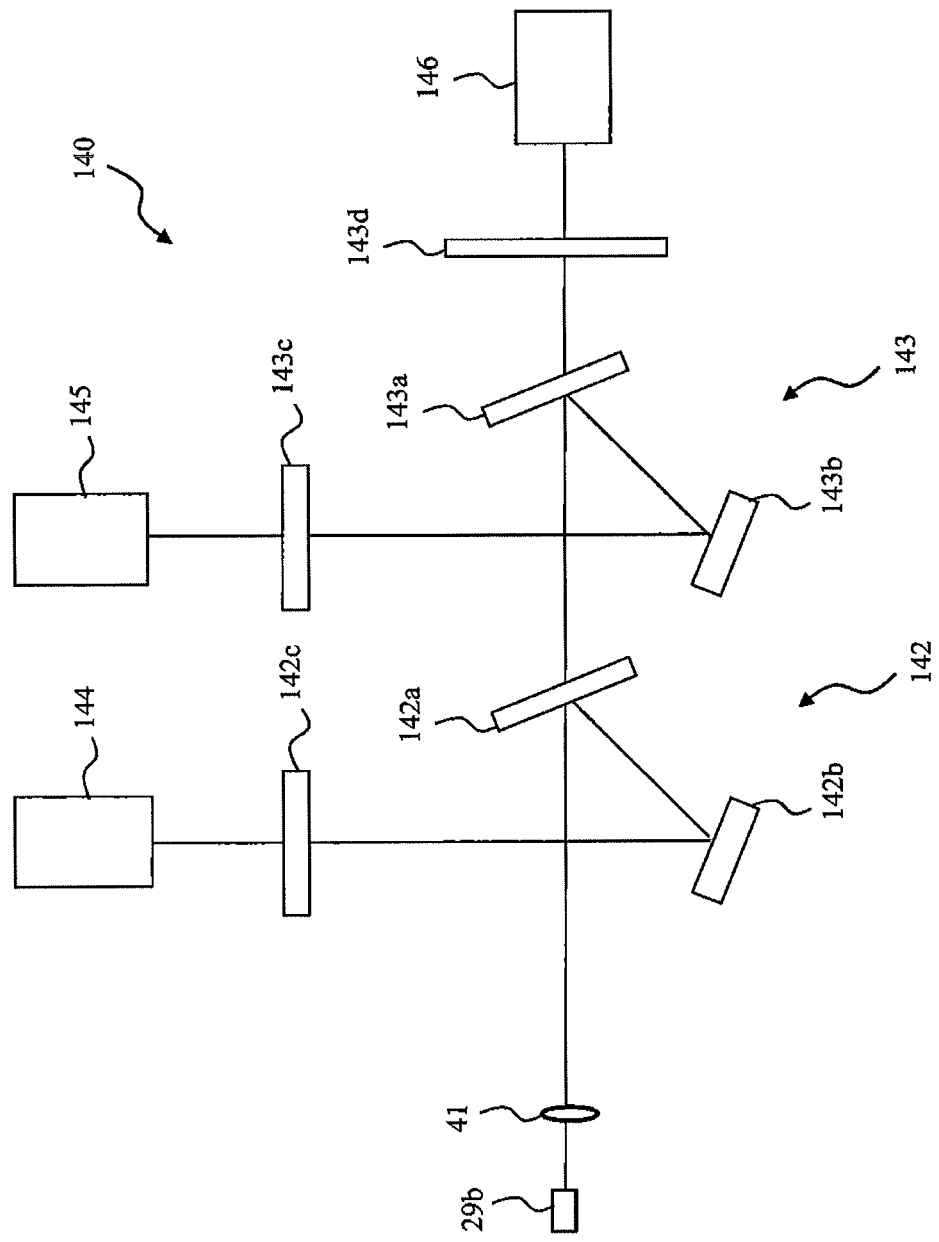
FIG. 7 is an explanatory drawing illustrating a configuration of a spectroscope according to a first exemplary embodiment.

First, using FIG. 7, a configuration of a spectroscope 140 according to a first exemplary embodiment is illustrated. The spectroscope 140 is configured of the collimating optical system 41 converting the signal light exiting out of the fiber coupler 29b into substantially collimated light flux, first and second spectroscopic optical systems 142 and 143 and first to third optical receivers 144 to 146. Moreover, the first spectroscopic optical system 142 is configured of a first optical element 142a which is arranged on the optical axis of the collimating optical system 41 and on which the substantially collimated signal light exiting out of the collimating optical system 41 is incident, a second optical element 142b reflecting the signal light reflected on the first optical element 142a, and an excitation light cutoff filter 142c cutting the excitation light included in the signal light reflected on the second optical element 142b. The first optical receiver 144 is disposed at the position where the signal light having passed through the excitation light cutoff filter 142c is incident thereon. Moreover, the second spectroscopic optical system 143 is configured of a first optical element 143a which is arranged on the optical axis of the collimating optical system 41 and on which the signal light having passed through the first optical element 142a of the first spectroscopic optical system 142 is incident, a second optical element 143b reflecting the signal light reflected on the first optical element 143a, and an excitation light cutoff filter 143c cutting the excitation light included in the signal light reflected on the second optical element 143b. The second optical receiver 145 is disposed at the position where the signal light having passed through the excitation light cutoff filter 143c is incident thereon. An excitation light cutoff filter 143d and the third optical receiver 146 are disposed at the positions where the signal light having passed through the first optical element 143a is incident thereon. Notably, in the spectroscope 140 according to the first exemplary embodiment, the first optical elements 142a and 143a of the first and second spectroscopic optical systems 142 and 143 are configured of long path filters which are angle-dependent elements, and moreover, the second optical elements 142b and 143b thereof are configured of mirrors.

The excitation light cutoff filters 142c, 143c and 143d may be any of conventional filters (long path filters or band-pass filters) which do not change in characteristics depending on an angle and angle-dependent elements. The angle-dependent element may be configured of one long path filter or one band-pass filter, or may be configured of a combination of one long path filter and one short path filter.

Notably, the short path filter has characteristics in which light with a shorter wavelength than the predetermined wavelength λ is transmitted and light with a longer wavelength than this wavelength λ is reflected. The band-pass filter has characteristics in which light in a predetermined wavelength region is only transmitted. Notably, the same holds true for a second exemplary embodiment and a third exemplary embodiment mentioned later.

Figure 8:
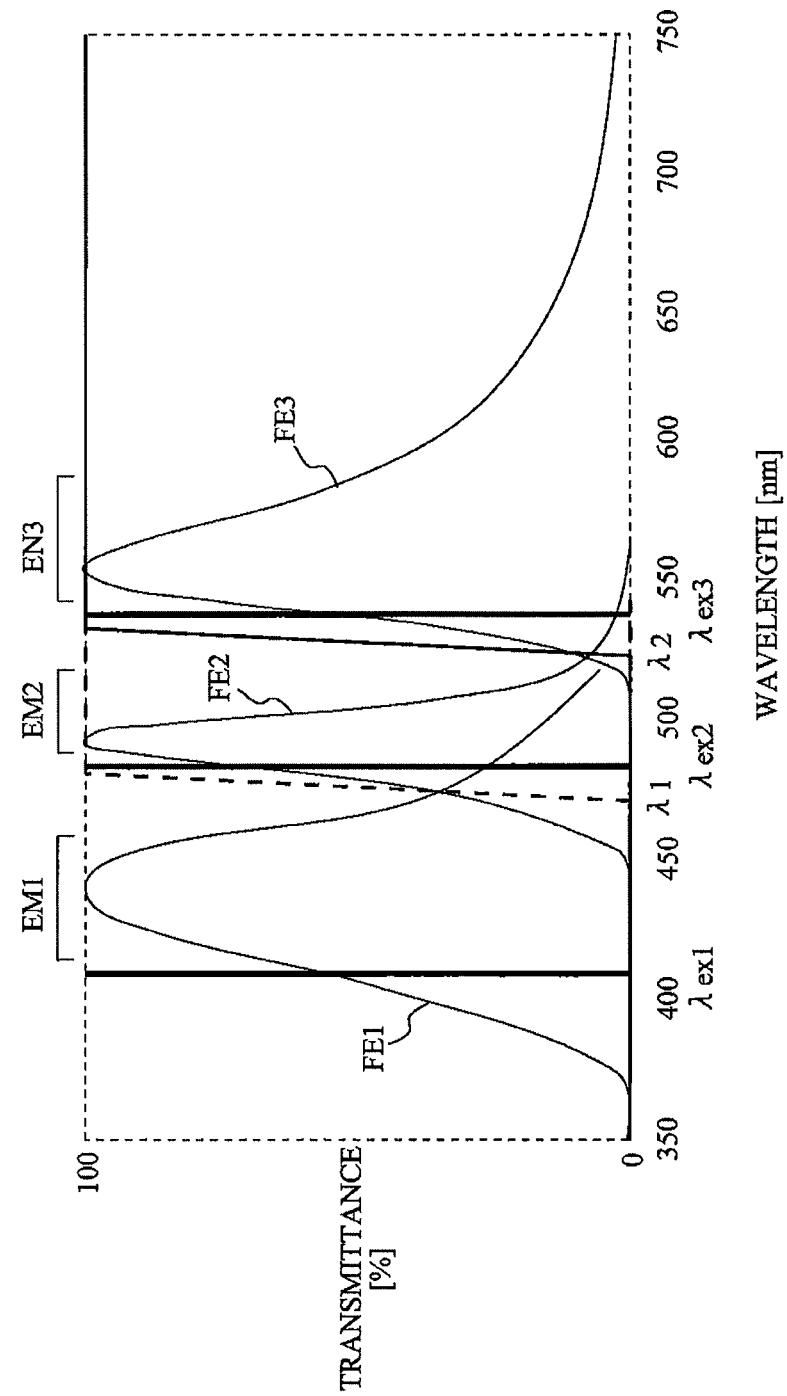
FIG. 8 is an explanatory drawing for explaining wavelength characteristics of the spectroscope according to the first exemplary embodiment.

The spectroscope 140 according to the first exemplary embodiment is configured to divide a wavelength region to be measured into three regions as illustrated in FIG. 8 using the two spectroscopic optical systems 142 and 143 (a region of shorter wavelength than λ1, a region of wavelength λ1 to λ2 and a region of longer wavelength than λ2 in the case where a boundary wavelength of the first optical element 142a of the first spectroscopic optical system 142 is λ1 and a boundary wavelength of the first optical element 143a of the second spectroscopic optical system 143 is λ2), and to detect light intensities for the regions with the first to third optical receivers 144 to 146, respectively. Herein, FIG. 8 illustrates relation between the boundary wavelengths λ1 and λ2 of the first spectral elements 142a and 143a of the first and second spectroscopic optical systems 142 and 143 configured with respect to rays of fluorescence light (referred to as FE1, FE2 and FE3) corresponding to respective rays of excitation light which arise in exciting three respective fluorescent dyes with the rays of excitation light having λex1=405 nm, λex2=514 nm and λex3=594 nm when the specimen is stained with the fluorescent dyes of DAPI, yellow fluorescent protein (YFP) and mCherry (triple staining). As apparent from FIG. 8, the wavelengths at which the intensities of the rays of fluorescence light FE1 to FE3 are at their maximums are larger than the wavelengths λex1 to λex3 of the rays of the excitation light for causing the respective rays of fluorescence light to arise. Therefore, when the boundary wavelengths λ1 and λ2 of the first optical elements 142a and 143a of the first and second spectroscopic optical systems 142 and 143 are configured to be shorter than λex2 and λex3, the rays of excitation light and the rays of fluorescence light for the three fluorescent dyes fall in the above-mentioned three regions, respectively. Furthermore, cutting the rays of excitation light for the respective regions with the excitation light cutoff filters 142c, 143c and 143d enables the intensities of the three rays of fluorescence light around their peaks to be detected with the first to third optical receivers 144 to 146.

FIG. 8 illustrates separation regions EM1 to EM3 of filters which are used for a conventional spectroscope and spectrally separate light in desired wavelength bands from the signal light and the conventional spectroscope can detect the fluorescence light only within the ranges thereof. On the contrary, according to the spectroscope 140 of the first exemplary embodiment, varying the angles of the first optical elements (long path filters) 142a and 143a of the first and second spectroscopic optical systems 142 and 143 with respect to the optical axis to vary the incident angles α of the signal light thereon enables the boundary wavelengths λ1 and λ2 to be shifted and an acquisition region of the fluorescence light to be widened arbitrarily. Moreover, even when the wavelength of the excitation light is shifted due to an error, rotating the excitation light cutoff filters 142c, 143c and 143d which are angle-dependent elements to vary the incident angles of the signal light thereon enables the wavelengths at which the removal is possible to be varied and adjusted. Notably, in the first exemplary embodiment above, while division into the three regions with the two spectroscopic optical systems is described, a configuration with one spectroscopic optical system may be applied or a configuration with four or more spectroscopic optical systems may be applied.

Second Exemplary Embodiment

Figure 9:
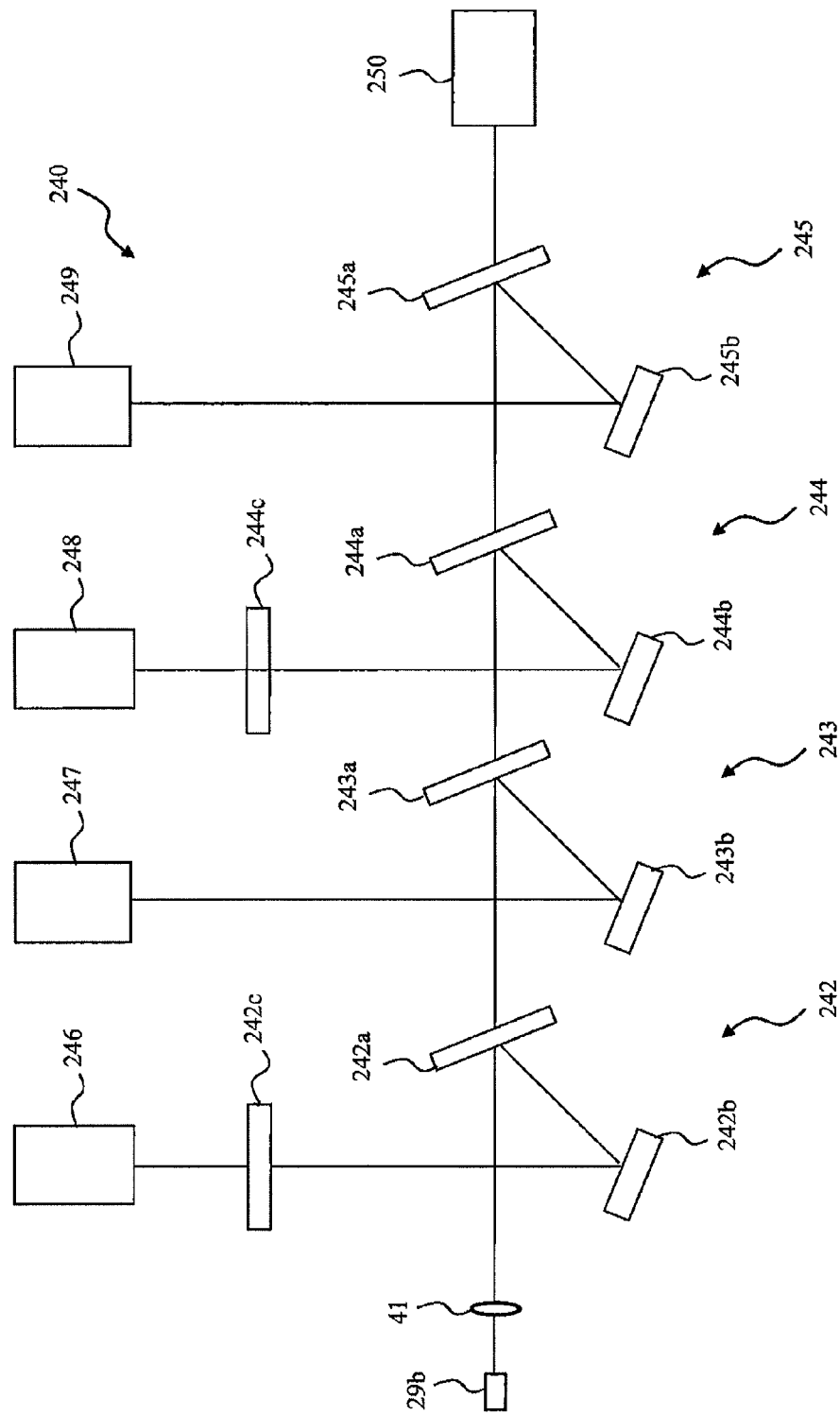
FIG. 9 is an explanatory drawing illustrating a configuration of a spectroscope according to a second exemplary embodiment.
Figure 10:
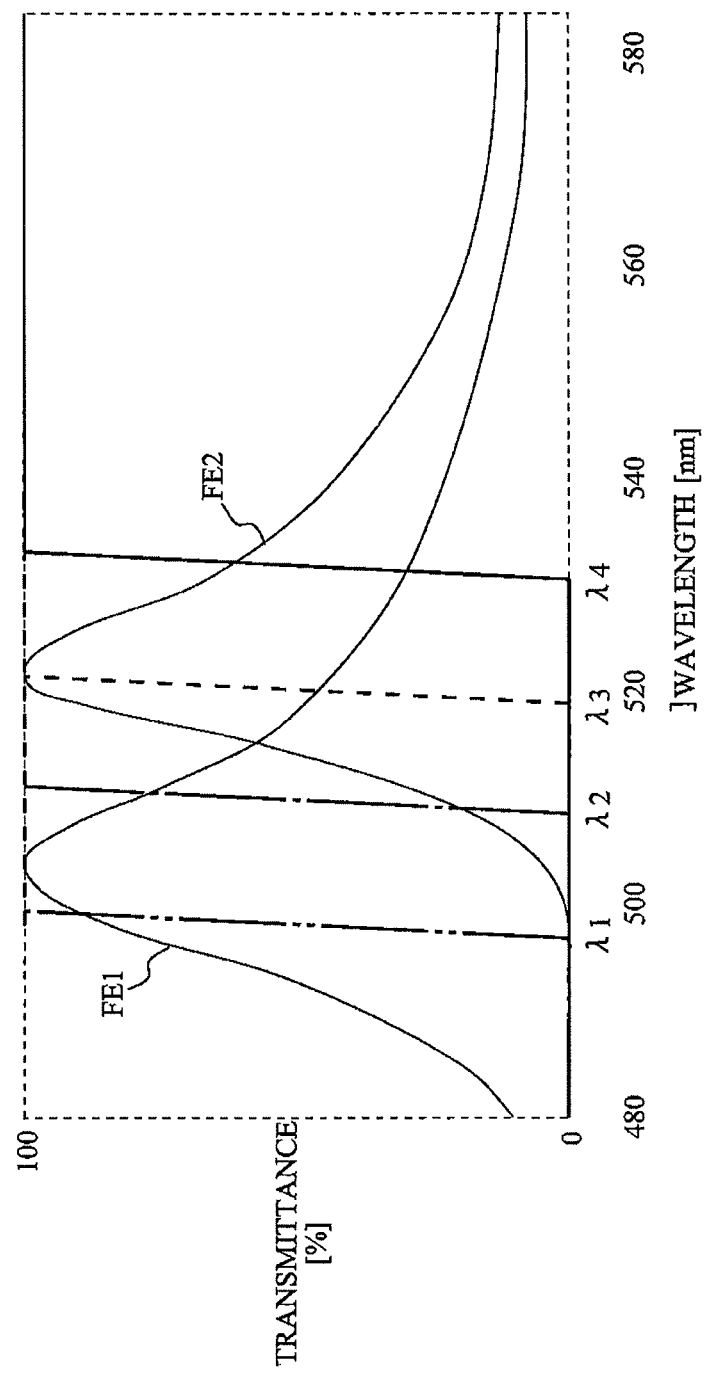
FIG. 10 is an explanatory drawing for explaining wavelength characteristics of the spectroscope according to the second exemplary embodiment.

FIG. 9 illustrates a configuration of a spectroscope 240 according to a second exemplary embodiment and a case where the spectroscope 240 is configured to spectrally separate the signal light for five wavelength regions with four spectroscopic optical systems 242 to 245 and detect light intensities for the regions with five respective optical receivers 246 to 250. Each of the spectroscopic optical systems 242 to 245 is the same as that in the above-mentioned first exemplary embodiment and they are configured of first optical elements 242a to 245a configured of long path filters which are angle-dependent elements and second optical elements 242b to 245b configured of mirrors. In this way, division into a plurality of wavelength regions and detection of light intensities for the respective regions enables peak separation of the signal light. For example, as illustrated in FIG. 10, even in the case of observation of two rays of fluorescence light FE1 and FE2 peaks of which are close to each other, dividing the wavelength region including the peaks into five regions enables peak separation. In this stage, rotating the first optical elements 242a to 245a individually to vary the incident angles of the signal light thereon enables boundary wavelengths λ1 to λ4 to be varied. Hence, the wavelength bands of the divided regions can be adjusted to match the measured peaks of fluorescence light. Notably, properly disposing excitation light cutoff filters 242c and 244c according to the excitation light enables the excitation light to be removed from the signal light. When the excitation light cutoff filters 242c and 244c are also angle-dependent elements, rotating them enables the wavelengths at which the removal is possible to be adjusted to match the wavelengths of the excitation light.

Third Exemplary Embodiment

Figure 11:
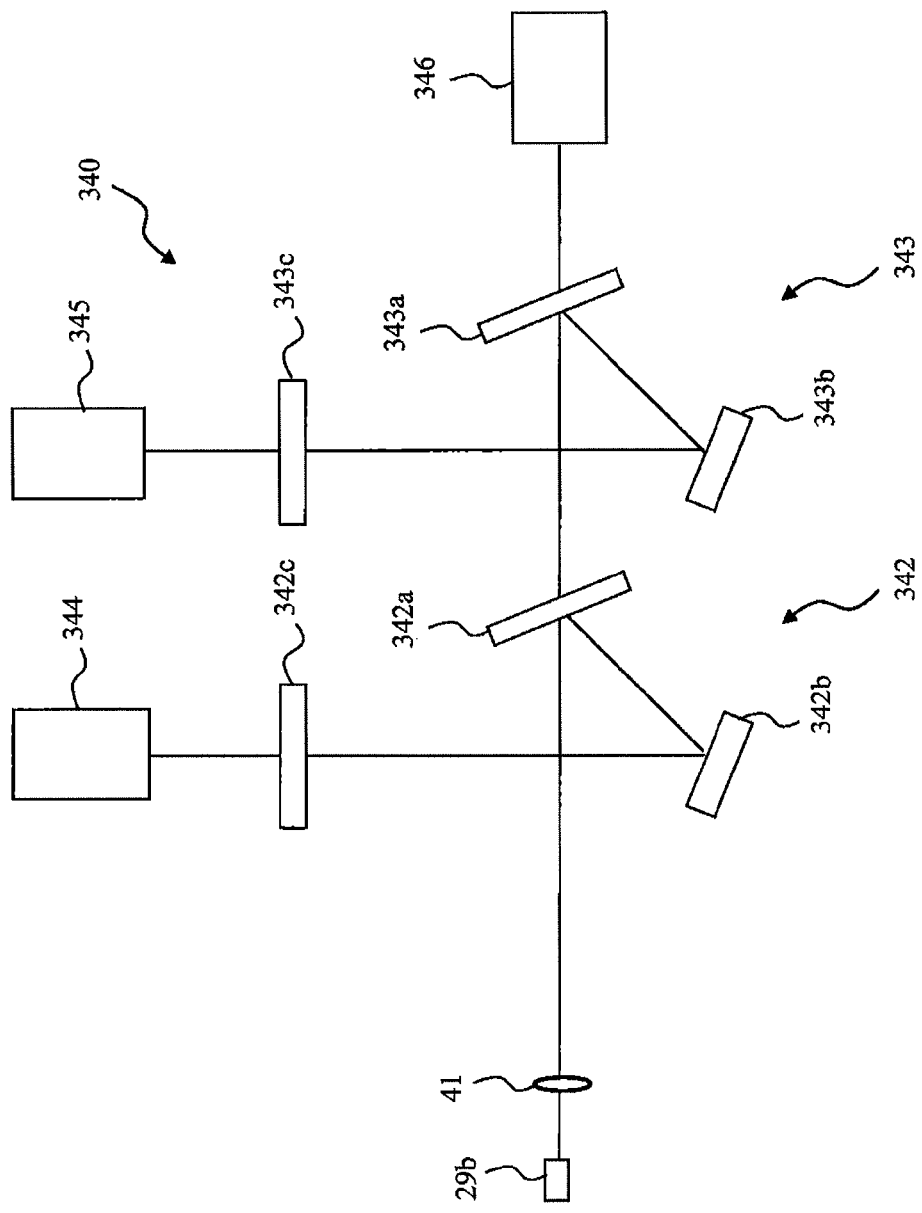
FIG. 11 is an explanatory drawing illustrating a configuration of a spectroscope according to a third exemplary embodiment.

FIG. 11 illustrates a configuration of a spectroscope 340 according to a third exemplary embodiment and a case where the spectroscope 340 is configured to spectrally separate the signal light for three wavelength regions with two spectroscopic optical systems 342 and 343 and to detect light intensities for the regions with three respective optical receivers 344 to 346. In the spectroscope 340, each of the first and second spectroscopic optical systems 342 and 343 is configured of two optical elements similarly to the first and second exemplary embodiments. First optical elements 342a and 343a are configured of sharp cutoff filters each of which absorbs light with wavelength not more than a certain one and transmits light with wavelength not less than that. The sharp cutoff filters are not angle-dependent elements and therefore the boundary wavelengths thereof are not varied if the first optical elements 342a and 343a are rotated. Meanwhile, second optical elements 342b and 343b are notch filters each of which transmits light in a predetermined narrow wavelength band and reflects the light with remaining wavelength and are configured as angle-dependent elements. Therefore, when the second optical elements 342b and 343b are rotated to vary the incident angles of the signal light thereon, the wavelength bands of light caused to pass through are varied. Moreover, in the first and second spectroscopic optical systems 342 and 343, excitation light cutoff filters 342c and 343c are disposed between the second optical element 342b of the first spectroscopic optical system 342 and the first optical receiver 344 and between the second optical element 343b of the second spectroscopic optical system 343 and the second optical receiver 345.

Figure 12:
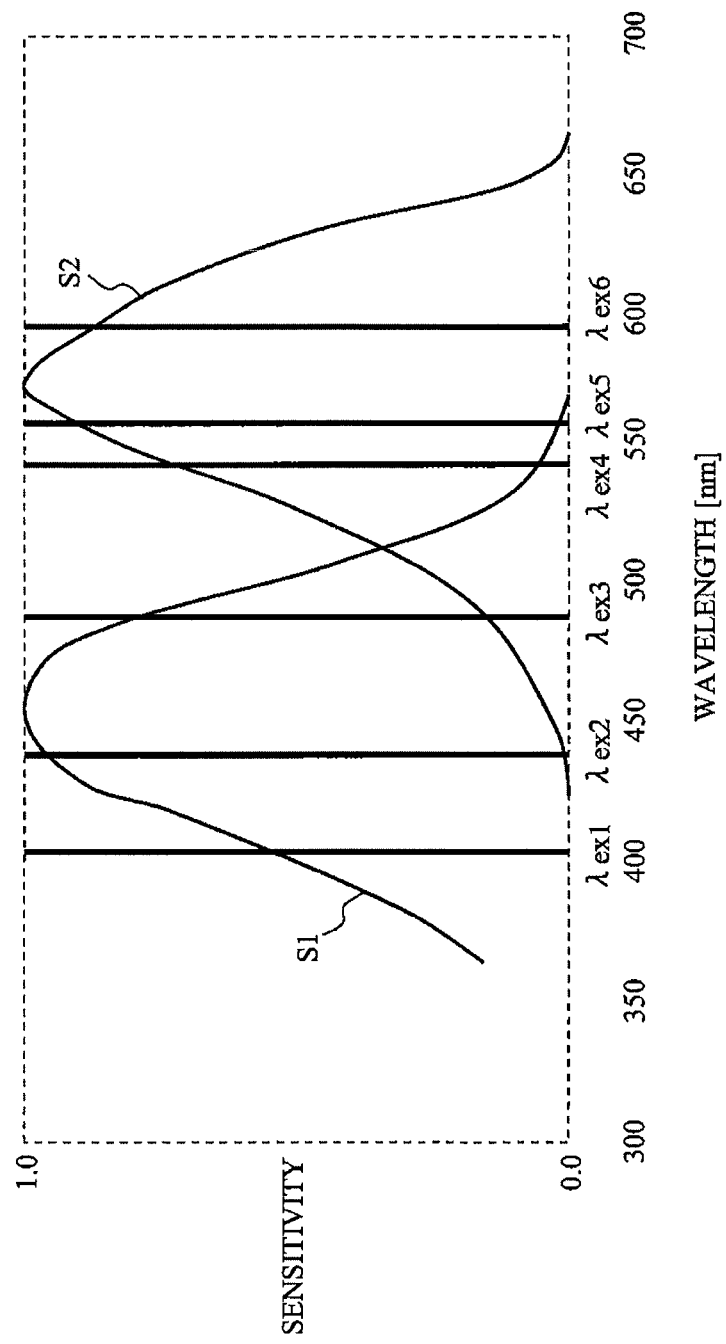
FIG. 12 is an explanatory drawing for explaining wavelength characteristics of the spectroscope according to the third exemplary embodiment.

FIG. 12 illustrates sensitivities at which the channel rhodopsin (CHR2) and halorhodopsin (NPHR) among proteins contained in the brain tells sense stimulation to stimulating light with wavelengths for them and illustrates a sensitivity curve S1 for CHR2 and a sensitivity curve S2 for NPHR. As apparent from FIG. 12, the stimulation wavelength only has different sensitivity depending on the wavelength and diverse. In other words, the stimulation wavelength desired by the user is diverse (for example, λex1 to λex6 illustrated in FIG. 12). A current filter is not practical to be operable for all of those.

The spectroscope 340 according to the third exemplary embodiment spectrally separates the signal light for three wavelength regions with the first optical elements 342a and 343a of the first and second spectroscopic optical systems 342 and 343 to perform detection thereof but cannot vary the boundary regions for those. Meanwhile, the second optical elements 342b and 343b have a function of allowing the stimulating light contained in the signal light spectrally separated with the first optical elements 342a and 343a to pass through and be removed. Rotating the second optical elements 342b and 343b to vary the incident angles thereon enables the wavelength band for the stimulating light which is allowed to pass through (removed) to be adjusted. Notably, irradiating the specimen that has been stimulated with the stimulating light with the excitation light causes it to radiate the fluorescence light. Hence, in order that the excitation light contained in the signal light reflected on the second optical elements (notch filters) 342b and 343b is not incident on the first and second optical receivers 344 and 345, as illustrated in FIG. 11, excitation light cutoff filters 342c and 343c are disposed. As above, according to the spectroscope 340 according to the third exemplary embodiment, varying the incident angles of the signal light on the second optical elements (notch filters) 342b and 343b enables wavelength shifting to arise and stimulation wavelength cutting desired by the user to be set arbitrarily. In the third exemplary embodiment, while two sets of spectroscopic optical systems are used, a configuration with three or more sets of those may be applied in the case where there are a plurality of stimulation wavelengths.

Fourth Exemplary Embodiment

Figure 13:
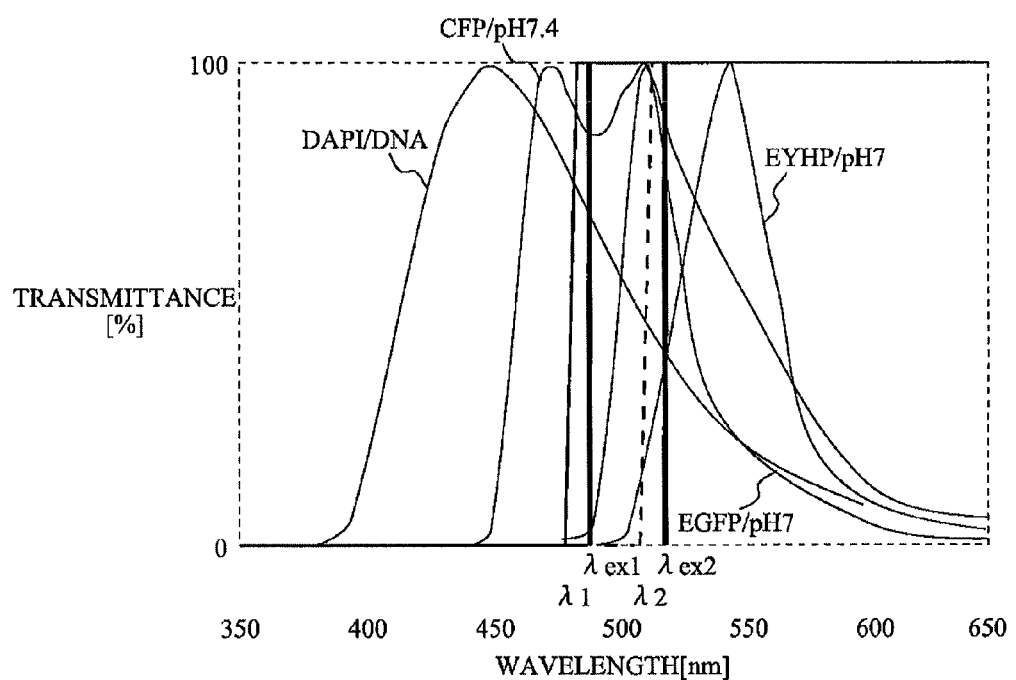
FIG. 13 is an explanatory drawing for explaining wavelength characteristics of a spectroscope according to a fourth exemplary embodiment.

As a fourth exemplary embodiment, using FIG. 13, rotational angles of spectral elements constituting a spectroscopic optical system in the occasion of observation with different combinations of fluorescent dyes. First, when dual-color fluorescence observation is performed with DAPI and enhanced green fluorescent protein (EGFP), the excitation wavelength λex1 of EGFP is 488 nm and, supposing that the tolerance of the laser device 11 is ±5 nm, configuring the boundary wavelength λ1 of the spectral element to be 485 nm enables fluorescence light of DAPI to be acquired within a range in which its excitation light is not incident. Meanwhile, when dual-color fluorescence observation is performed with cyan fluorescent protein (CFP) and enhanced yellow fluorescent protein (EYFP), the excitation wavelength $\lambda ex2$ of EYFP is 514 nm and, supposing that the tolerance of the laser device 11 is ±5 nm, configuring the boundary wavelength $\lambda 2$ of the spectral element to be 511 nm enables fluorescence light of CFP to be acquired within a range in which its excitation light is not incident. As above, when fluorescence light emitted from one fluorescent dye is separated from fluorescence light emitted from the other fluorescent dye in dual-color fluorescence observation, while the case of using a conventional filter cube causes the filter to be exchanged, the configuration, as in the abovementioned embodiments, in which the spectral elements of the spectroscopic optical systems are rotated to vary the incident angles of the signal light thereon enables the boundary wavelengths to be varied simply due to rotation of the spectral elements. In the case of the fourth exemplary embodiment, rotating the spectral elements by 18 degrees enables the boundary wavelengths $\lambda 1$ and $\lambda 2$ to be switched. Moreover, adjustment of the boundary wavelengths is enabled as above, and thus, the boundary wavelengths can be configured to be close to the wavelength of the excitation light and the fluorescence light from the specimen can be acquired as efficiently as possible.

In addition, the requirements of the respective embodiments described above may be appropriately combined. In addition, there are cases where some constituent elements may not be used. In addition, all the publications and the disclosures of U.S. patents regarding a device and the like cited in the respective embodiments described above and modified examples are incorporated herein by reference to the extent permitted by law.

REFERENCE SIGNS LIST

1 Microspectroscopic system
40, 140, 240 and 340 Spectroscopes
41 Collimating optical system
42, 43, 142, 143, 242 to 245, 342 and 334 Spectroscopic optical systems
42a, 43a, 142a, 143a, 242a to 245a, 342a and 343a First optical elements
42b, 43b, 142b, 143b, 242b to 245b, 342b and 343b Second optical elements
142c, 143c, 143d, 242c, 244c, 342c and 343c Excitation light cutoff filters (barrier filters)
44 to 46, 144 to 146, 246 to 250 and 344 to 346 Optical receivers
50 Controller unit
51 Input unit
53 Storage unit
54a to 54d Drive units (mechanisms)

The invention claimed is:

1. A spectroscope comprising:
a first optical element that transmits incident light within a first wavelength region and reflects the incident light within a second wavelength region, the first and second wavelength regions varying relative to an incident angle of the incident light relative to an incident surface of the first optical element on which the incident light is received;
a detector that detects light transmitted through or reflected by the incident surface of the first optical element;
a first drive mechanism that moves the first optical element; and
a controller that controls the first drive mechanism to vary a direction of the incident surface of the first optical element.

2. The spectroscope according to claim 1, further comprising a second optical element that guides the light transmitted through or reflected by the first optical element to the detector.

3. The spectroscope according to claim 2, wherein the second optical element is configured of a mirror.

4. The spectroscope according to claim 2, further comprising a second drive mechanism that moves the second optical element, wherein the controller controls the second drive mechanism to vary a direction of an incident surface of the second optical element on which the light transmitted through or reflected by the first optical element is received.

5. The spectroscope according to claim 4, wherein the controller controls the first drive mechanism to vary the direction of the incident surface of the first optical element and the second drive mechanism to vary the direction of the incident surface of the second optical element, respectively, while maintaining an angle formed by a plane extending from the incident surface of the first optical element and a plane extending from the incident surface of the second optical element.

6. The spectroscope according to claim 5, wherein the controller controls the first drive mechanism to vary the direction of the incident surface of the first optical element and the second drive mechanism to vary the direction of the incident surface of the second optical element, respectively, by rotating the first optical element and the second optical element about a line of intersection of the plane extending from the incident surface of the first optical element and the plane extending from the incident surface of the second optical element.

7. The spectroscope according to claim 6, wherein the controller controls the first drive mechanism to vary the direction of the incident surface of the first optical element and controls the second drive mechanism to vary the direction of the incident surface of the second optical element, respectively, by rotating the first optical element to a predetermined position and moving a position of the second optical element.

8. The spectroscope according to claim 7, further comprising a condenser lens that collects the light reflected by the second optical element on the detector.

9. The spectroscope according to claim 1, further comprising a barrier filter that is disposed between the first optical element and the detector, wherein a wavelength band of light that is cut by the barrier filter varies relative to an incident angle of incident light received by the barrier filter.

10. The spectroscope according to claim 1, further comprising a detector drive mechanism that moves the detector, wherein the controller controls the detector drive mechanism to move the detector.

11. A microspectroscopic system comprising:
a scanning mirror;
an objective lens; and
the spectroscope according to claim 1.

12. A microspectroscopic system comprising:
a scanning mirror;
an objective lens; and
a spectroscope, wherein
the microspectroscopic system irradiates a specimen containing a fluorescent substance with light radiated from a light source and spectrally separates the light emitted from the specimen, and the spectroscope comprises:
- a first optical element that transmits incident light within a first wavelength region and reflects the incident light within a second wavelength region, the first and second wavelength regions varying relative to an incident angle of the incident light relative to an incident surface of the first optical element on which the incident light is received;
- a detector that detects light transmitted through or reflected by the incident surface of the first optical element;
- a first drive mechanism that moves the first optical element; and
- a controller that controls the first drive mechanism to vary a direction of the incident surface of the first optical element.

13. The microspectroscopic system according to claim 12, wherein the controller controls the first drive mechanism relative to at least one of a kind of a fluorescent dye in the specimen, a wavelength of the light with which the specimen is irradiated and a wavelength of the light emitted from the specimen.

14. The microspectroscopic system according to claim 13, further comprising a storage unit that stores the incident angle that corresponds to the at least one of the kind of the fluorescent dye, the wavelength of the light with which the specimen is irradiated and the wavelength of the light emitted from the specimen, wherein the controller controls the first drive mechanism based on the information read out from the storage unit.

15. The microspectroscopic system according to claim 13, wherein the controller controls the first drive mechanism based on a correction value of the incident angle that arises from switching a wavelength of the light radiated from the light source.

* * * * *